United States Patent [19]

Pierce

[11] Patent Number: 5,045,076

[45] Date of Patent: Sep. 3, 1991

[54] DISPOSABLE INSULATED SURGICAL BASINS

[76] Inventor: Pam Pierce, 14163 Mandy La., Tyler, Tex. 75703

[21] Appl. No.: 498,847

[22] Filed: Mar. 26, 1990

[51] Int. Cl.⁵ ............................................. A61M 1/00
[52] U.S. Cl. .................................. 604/317; 604/319; 604/321; 604/403
[58] Field of Search ............................ 604/403–408, 604/317–321; 215/DIG. 3; 222/572

[56] References Cited

U.S. PATENT DOCUMENTS

| | | | |
|---|---|---|---|
| 3,032,037 | 5/1962 | Huber | 604/319 X |
| 3,380,489 | 4/1968 | Harautuneian | 604/403 X |
| 4,234,095 | 11/1980 | Safianoff | 604/405 X |
| 4,347,946 | 9/1982 | Nichols | 604/319 X |
| 4,449,984 | 5/1984 | Cruz | 604/317 X |
| 4,516,973 | 5/1985 | Telang | 604/319 |
| 4,551,141 | 11/1985 | McNeil | 604/317 |
| 4,642,093 | 2/1987 | Härle | 604/404 X |
| 4,880,411 | 11/1989 | Fangrow, Jr. et al. | 604/319 X |
| 4,895,275 | 1/1990 | Quinn et al. | 604/407 X |
| 4,957,224 | 9/1990 | Kessler et al. | 222/572 X |
| 4,957,492 | 9/1990 | McVay | 604/319 |

Primary Examiner—Robert A. Hafer
Assistant Examiner—Kerry Owens
Attorney, Agent, or Firm—Ronald B. Sefrna

[57] ABSTRACT

The present invention provides disposable insulated basins constructed of materials suitable for sterilization, particularly useful in human surgical and other medical procedures. The invention specifically provides a surgical irrigation basin having a hollow, insulated bowl-like body, an insulated cover adapted to be attached to the body in liquid-tight relation, and a flanged tube extending from the exterior of the basin to the interior thereof to receive and retain an irrigation syringe. The body and the cover are formed of double wall construction with insulating material sandwiched and sealed between the walls. In the preferred embodiment the insulation comprises a nonwoven fabric bonded between two thin sheets of flexible plastic coated on at least one side with reflective material. Various alternative embodiments and modifications from the preferred embodiment are also provided.

16 Claims, 3 Drawing Sheets

DISPOSABLE INSULATED SURGICAL BASINS

FIELD OF THE INVENTION

The present invention generally relates to fluid containers useable in the medical field, and in its preferred embodiments more specifically relates to sterile, disposable, insulated fluid containers intended for use in conjunction with human medical care, especially surgical procedures, and there especially for the holding and dispensing of warmed surgical irrigation solutions.

BACKGROUND OF THE INVENTION

In the course of performing surgical operations on human patients it is common practice to periodically irrigate the incision and exposed areas of the body cavity with a warmed sterile irrigation solution. Commercially prepared irrigation solutions with added antibiotics or other drugs are commonly used for that purpose. In typical practice, one or more bottles of the irrigation solution to be used are warmed outside the operating room, individually transported into the operating room, and poured into a sterile, open, uninsulated basin that is place on the sterile field in the operating room. The irrigation solution is typically applied with a large sterile syringe, kept in close proximity to or placed within the basin of irrigation solution.

This typical procedure presents several problems and disadvantages. Since the basins used within the operating room are neither covered nor insulated, the irrigation solution cools rapidly to a temperature below that suitable for use, and it is often necessary to replenish or replace the irrigation solution solely in order to elevate its temperature, which is not only wasteful and expensive, especially if durgs have been added to the irrigation solution, but may result in unavailability of useable irrigation solution at a critical point in the surgical procedure. The cooling problem is particularly severe when the holding basins are constructed of metal, since heat may be rapidly dissipated through the basin wall as well as from the exposed liquid surface. The need for frequent replacement of the solution imposes an additional burden on the surgical staff, and the necessity of bringing the replacement solution from outside the operating room increases the risk of compromising sterility. The use of uncovered basins increases the risk that the solution may be spilled if the basin is tipped. Further, the surgical basins used for holding the irrigation solution at the operating table do not provide a means of holding the irrigation syringe, which is often loosely placed within the basin in an upside down position.

No coordinated approach to solution of these problems and disadvantages is known in the prior art. The use of insulated containers for the purpose of maintaining fluid temperature at or near a desired level is known, as illustrated by U.S. Pat. No. 3,048,294 to Osborn, et.al., as is the use of insulating jackets for existing containers, as illustrated by U.S. Pat. No. 4,039,098 to Stilts. The general insulated container art does not, however, address convenint retention of an irrigation syringe nor does it address the factor of sterility, which is of extreme importance in many aspects of medical practice, especially in a surgical operating room environment.

The use of closed containers having some form of pouring spout or limited entry point is also known in the prior art for some uses, as illustrated by U.S. Pat. No. 3,414,165 to Goodenow, U.S. Pat. No. 3,490,501 to Manem, et.al., and U.S. Pat. No. 4,311,492 to Eltvedt. However, none of the known references teach the use of a spout or flange arrangement specifically adapted to the combination of uses most appropriate for an irrigation solution basin, including pouring of liquid into the container, pouring of liquid from the container, and receiving an irrigation syringe for access to the liquid as well as retaining the syringe in a stable position relative to the container.

Accordingly, there remains a need for closed, heat-retaining, insulated medical-use basins, a need for such basins adapted to readily receive and dispense liquids, and a need for such basins further adapted to receive and retain a syringe used for the drawing of liquid therefrom.

SUMMARY OF THE INVENTION

The present invention provides covered, fully insulated surgical basins for greatly improved heat retention, which may be readily sterilized and are completely disposable for control of disease vector transmission. In one of its embodiments the invention provides a means for holding an irrigation syringe ina conveniently accessible position, for withdrawing solution from the basin without removal of the cover, and for adding solution to the basin without removal of the cover.

In general, each of the basins of the invention comprises a hollow body with a continuous side wall, a bottom closure interconnected to or integrally formed with the side wall, and an open top. In some of the embodiments of the invention the upper edge of the side wall of the basin is adapted to receive a generally planar lid in removeable, liquid-tight relation. In one such embodiment, intended primarily for use as an operating table irrigation basin, a flanged tube is provided in the lid of the basin, forming a passageway to its interior for the dual purpose of insertion of the irrigation syringe for holding and for withdrawing solution, and of pouring fresh solution into the basin without removing the cover. In other embodiments the flanged tube may be disposed at the rim of the basin in the opening defined by the upper edge thereof, with the lid of that embodiment contoured to match the contour of the rim and flanged tube, or may be disposed in the side wall of the basin below the upper edge of the basin side wall. The flanged tube may extend into the interior of the basin to a point near the bottom closure, or may terminate in the interior at or near the point of entry into the interior.

The body of each basin, including the side wall and the bottom closure, may be formed of double wall construction, with an inner wall and an outer wall slightly separated therefrom, and an insulating material disposed between the two walls. The edges of the inner and outer walls are fully sealed to completely separate the intervening space and insulating material from the outside environment. Similarly, the cover for each basin may be of double wall construction, with an insulating material disposed and sealed between the two walls forming the cover. In the preferred embodiment of the invention, the insulating material comprises a thin nonwoven flexible fabric material with a thin reflective material, such as a reflectively coated plastic film of polyester or the like, bonded to at least one face, and preferably both faces, of the fabric material. Since the insulating material is fully sealed between the two walls of each component, the basin is adaptable to some uses for which it is not essential that the insulating material be sterile or susceptible to sterilization, and it will be understood that a wide range of alternative insulating materials may be employed.

The structure and features of the preferred and certain alternative embodiments of the basins of the invention will be described in more detail with reference to the accompanying drawing figures.

DETAILED DESCRIPTION OF PREFERRED AND ALTERNATIVE EMBODIMENTS OF THE INVENTION

Figure 1:
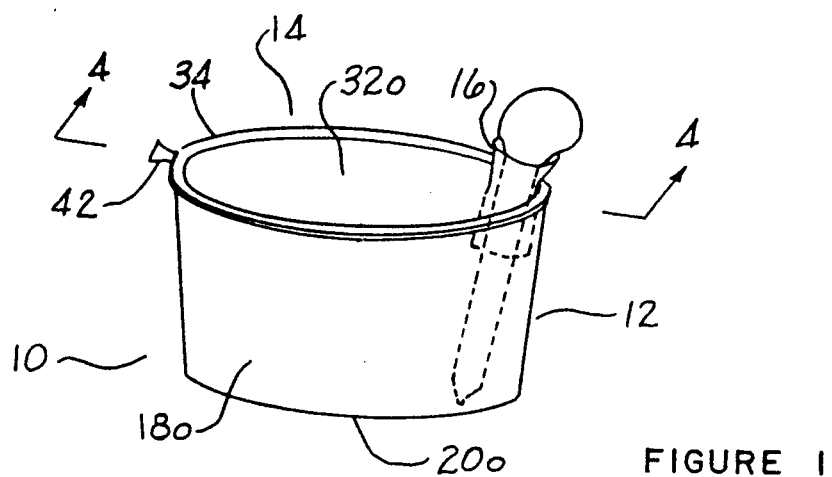
FIG. 1 is a perspective view of the preferred embodiment of the surgical irrigation basin of the invention with a typical irrigation syringe in place therein.
Figure 2:
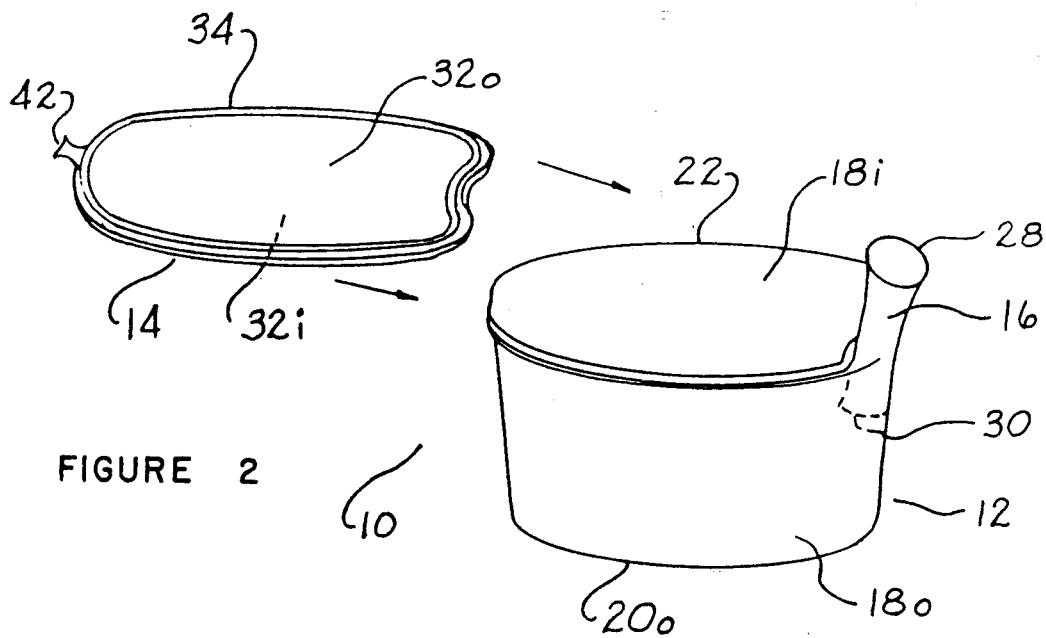
FIG. 2 is a perspective view of a first alternative embodiment of the surgival irrigation basin of the invention, with the cover slightly removed therefrom.
Figure 3:
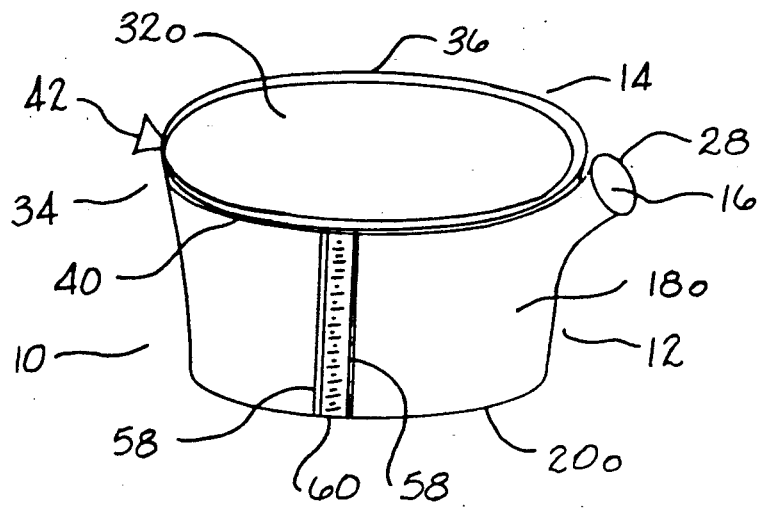
FIG. 3 is a perspective view of a second alternative embodiment of the surgical irrigation basin of the invention.

With reference to the accompanying drawings, especially FIGS. 1 through 3, the surgical irrigation basin embodiment of the invention, generally designated by reference numeral 10, will be seen to comprise the basic components of body 12, lid 14, and flanged tube 16.

Body 12 comprises a hollow structure, open at its top, including a continuous side wall 18 and a bottom closure 20 interconnected to the lower edge of side wall 18 in liquid-tight relation. In the preferred embodiment, the configuration of body 12 in a plane perpendicular to bottom closure 20 is oval, though other configurations, such as circular, may be used without departing from the scope of the invention. Side wall 18 is preferably inclined outwardly at a slight angle to the perpendicular from its interconnection to bottom closure 20 toward its upper edge 22, but alternative configurations such as perpendicular or inwardly inclined may also be employed.

In the preferred embodiment of body 12, side wall 18 is of double wall construction, having an outer wall 18o and an inner wall 18i, defining space 24 therebetween. It is preferred that bottom closure 20 also be of double construction, having an outer bottom 20o and an inner bottom 20i, with outer bottom 20o interconnected to outer wall 18o and with inner bottom 20i interconnected to inner wall 18i such that space 24 extends continuously between the respective inner and outer components of side wall 18 and bottom closure 20. Upper edge 22 of side wall 18 extends over the respective upper edges of outer and inner walls 18o and 18i as described in more detail below, sealing space 24 from the external environment. The creation of space 24 by outer and inner walls 18o and 18i, and by outer and inner bottom closures 20o and 20i, provides an insulating barrier against the transfer of heat from the contents of basin 10 through side wall 18 and bottom closure 20 so that such contents will remain at a useable temperature for a longer period of time than would be possible without such a barrier. Although it is preferred that space 24 extend through bottom closure 20 as well as side wall 18, it will be understood that the heat lost through bottom closure 20 will be less than the heat lost through side wall 18, and bottom closure 20 may be of single wall construction without significant impairment of insulating efficiency. It is further preferred that space 24, whether extending through bottom closure 20 or confined to side wall 18, be filled with insulating material, designated as body insulation 26, to increase the insulating efficiency.

In the preferred embodiment of basin 10 illustrated in FIG. 1, flanged tube 16 is disposed in and extends through lid 14 near the edge thereof, creating a passageway through lid 14 from the exterior of basin 10 to the interior thereof. It will be understood that alternative placements of tube 16 relative to body 12 may readily be employed, as indicated by the examples of FIG. 2 and FIG. 3. In a first alternative embodiment shown in FIG. 2, tube 16 is interconnected to the inner surface of side wall 18 with a portion of the length of flanged tube 16 in the interior of body 12 and a portion extending upwardly beyond upper edge 22 of side wall 18, and in a second alternative embodiment illustrated in FIG. 3, tube 16 extends through side wall 18 below upper edge 22. The configurations illustrated in FIGS. 2 and 3 both allow lid 14 to be removed from body 12 without removing or disturbing an irrigation syringe placed in tube 16. The configuration illustrated in FIG. 3 simplifies the attachment of lid 14 to body 12, but has the disadvantage of somewhat lower inherent stability due to the positioning of the mass of an irrigation syringe farthest from the center of basin 10.

Figure 4:
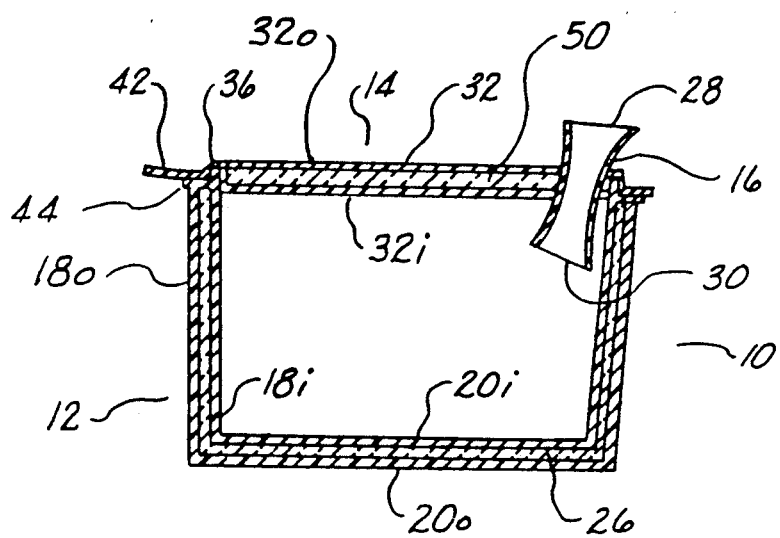
FIG. 4 is a sectioned elevation view of the body of the preferred embodiment of the surgical irrigation basin of the invention, along line 4—4 of FIG. 1.

Flanged tube 16 comprises an elongate hollow tube with a first, or upper, end 28 and a second, lower, end 30. In the preferred embodiment, upper end 28 is flared outwardly, forming a flange to receive and support a portion of the bulb of a typical irrigation syringe, as shown in FIG. 1, and to facilitate pouring of irrigation solution into body 12. Lower end 30 may also be flared slightly as indicated in FIGS. 1 and 4, to allow some freedom of movement of the irrigation syringe within tube 16 and to facilitate pouring of liquid from the interior of body 12 through tube 16, or lower end 30 may be formed as a straight extension of the intermediate portion of tube 16. In the preferred embodiments of the surgical irrigation basin of the invention, the distance of extension of tube 16 above the upper edge of side wall 18 is minimized in order to maximize the stability of basin 10 in use, consistent with the object of retaining the irrigation syringe in a convenient position to be readily grasped for use. In the preferred and alternative embodiments the height of side wall 18 of body 12 and the distance of extension of upper end 28 of tube 16 from side wall 18 are cooperatively adapted to approximately equal the length of the irrigation syringe to be used with basin 10 from the lower portion of its bulb to its tip, so that the tip of the irrigation syringe extends to or very near bottom closure 20 with its barrel extending through the interior of tube 16 and with its bulb resting in flared upper end 28. In the preferred embodiment of tube 16, as illustrated in FIG. 1, lower end 30 does not extend, or extends only a short distance, into the interior of basin 10 to facilitate pouring of irrigation solution from basin 10.

Figure 7:
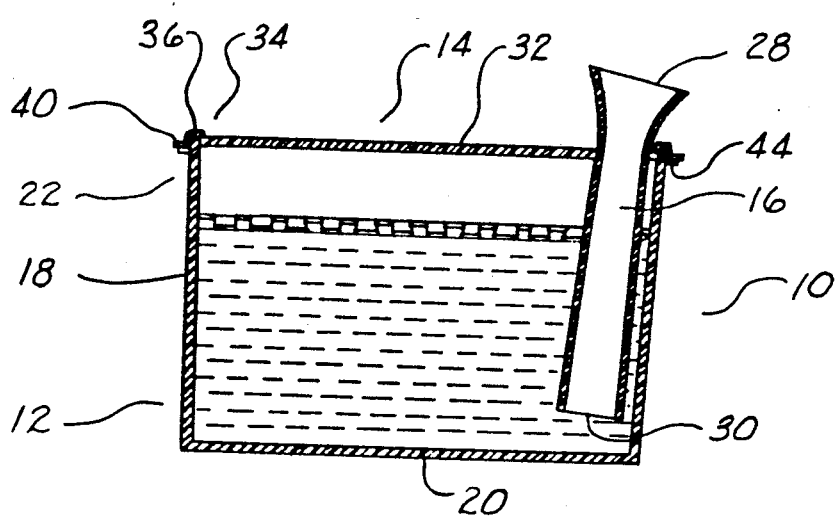
FIG. 7 is a sectioned elevation view of an uninsulated surgical irrigation basin of the invention illustrating an alternative configuration of the flanged tube of the basin.
Figure 8:
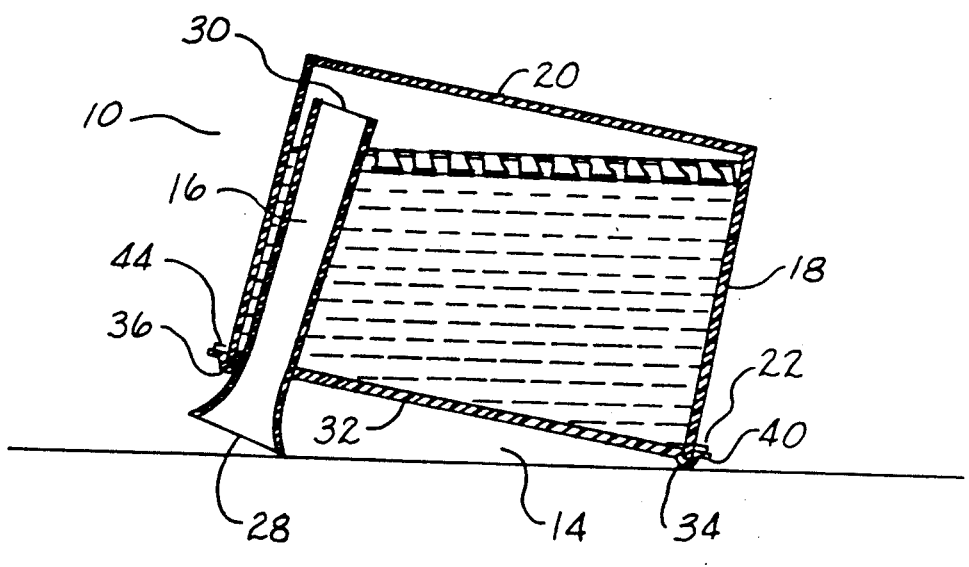
FIG. 8 is a sectioned elevation view an alternative single wall insulated surgical irrigation basin having the tube configuration of FIG. 7, with liquid therein, inverted upon a supporting surface.
Figure 9:
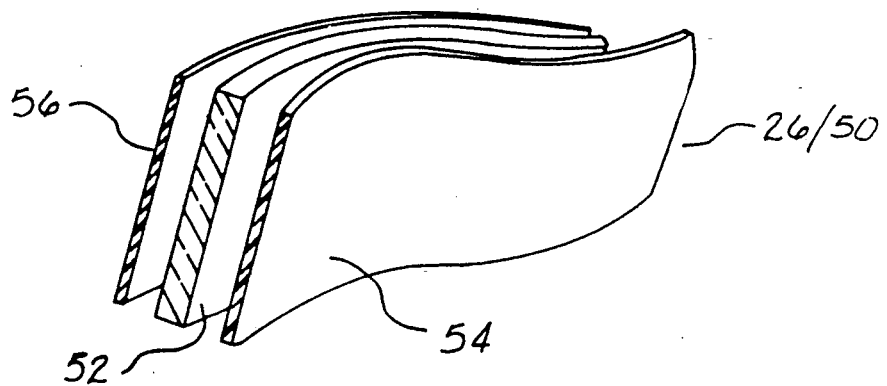
FIG. 9 is a partial perspective view of the preferred insulation component of the invention, partially separated.

In an alternative approach, illustrated in FIGS. 7 and 8, the length of the portion of tube 16 below the upper edge of side wall 18 is increased so that lower end 30 of tube 16 terminates near bottom closure 20 with only a small space therebetween. With basin 10 in an upright position, liquid is free to flow into the space between lower end 30 of tube 16 and bottom closure 20 and is readily accessible to be drawn into an irrigation syringe regardless of the level of liquid in basin 10, as evident from FIG. 7. In the event that basin 10 is overturned, as illustrated in FIG. 8, only a small amount of liquid, if any, will escape from the interior of basin 10 before the liquid level drops below end 30 of tube 16. Although illustrated with tube 16 extending through lid 14 in the preferred manner of FIG. 1, the same result may be achieved by extension of the length of tube 16 in the alternative dispositions depicted in FIGS. 2 and 3.

Figure 6:
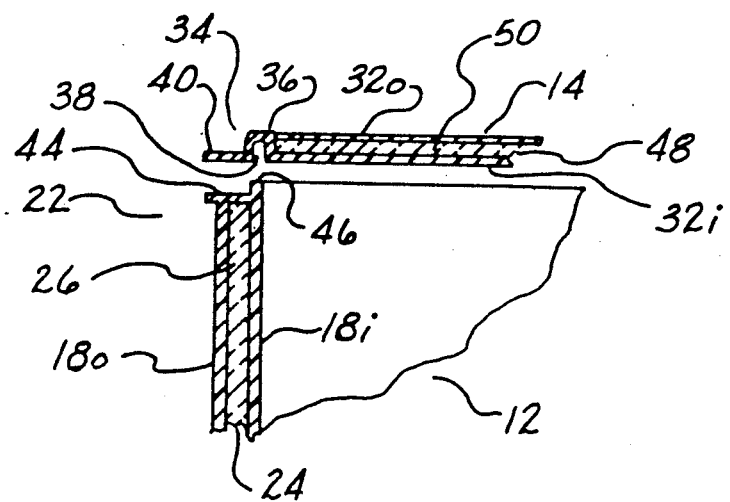
FIG. 6 is a partial, sectioned view the upper edge of the preferred construction of the side wall of a basin of the invention and the outer edge of the preferred construction of the lid component, slightly separated from the upper edge of the side wall.

Lid 14 of basin 10 comprises a substantially planar structure having a central portion 32 and an outer edge 34, adapted to be removeably interconnected to body 12 in liquid-tight relation. In the preferred embodiment, as illustrated in FIG. 6, outer edge 34 includes dome 36 integrally formed with central portion 32 and extending continuously around the perimeter of lid 14, defining continuous slot 38 under dome 36. Outer edge 34 further includes flange 40 extending continuously around the perimeter of lid 14 and outwardly from dome 36 in the plane of central portion 32.

Figure 5:
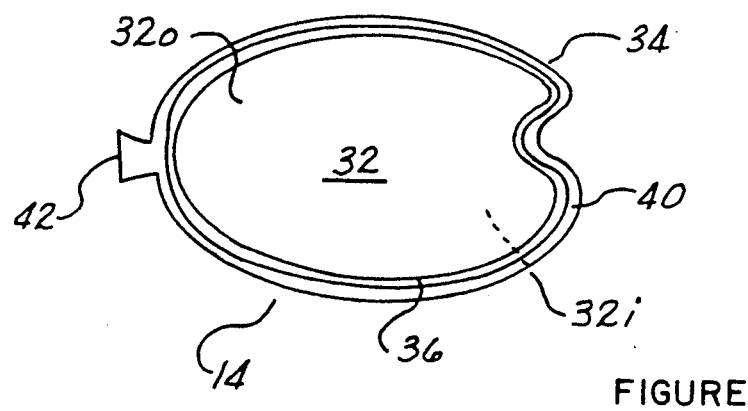
FIG. 5 is a plan view of the lid component of the first alternative embodiment of the surgical irrigation basin of the invention.

In the preferred embodiment of basin 10 shown in FIG. 1, tube 16 extends through an aperture penetrating central portion 32 of lid 14 and is interconnected thereto in liquid-tight relation. As shown in FIG. 5, the lid 14 for use with the surgical irrigation basin of FIG. 2 is contoured to match the curvature defined by the interconnected upper end 22 of side wall 18 and tube 16. When lid 14 is adapted for use with the surgical irrigation basin embodiment illustrated in FIG. 3, in which tube 16 extends through side wall 18 of body 12 below upper edge 22, no such contour adjustment is necessary. Lid 14 may further include finger tab 42 to facilitate removal of lid 14 from body 12. Finger tab 42, if used, may be disposed in the position illustrated, or may be disposed at any other convenient point on lid 14.

The structure of upper edge 22 of side wall 18 is adapted to mate with outer edge 34 of lid 14 in liquid-tight relation. In the preferred embodiment, illustrated in detail in FIG. 6, the upper edge of inner wall 18$i$ extends upwardly beyond the upper edge of outer wall 18$o$ and lip 44 extends around and outwardly from side wall 18$i$ a short distance below the top of inner wall 18$i$, over the top of outer wall 18$o$, to which lip 44 is interconnected. The upper end of inner wall 18$i$ forms mating ring 46 above lip 44. When lid 14 is attached to body 12, mating ring 46 is received tightly within slot 38 and the lower surface of flange 40 is received against the upper surface of lip 44, forming a liquid-tight seal between lid 14 and body 12. It is preferred that flange 40 extend outwardly a short distance beyond the outer edge of lip 44, to facilitate lifting of lid 14 from body 12. In the embodiment of basin 10 illustrated in FIG. 2, lip 44 and mating ring 46 extend around the outer surface of tube 16, with lip 44 interconnected between tube 16 and mating ring 46 and mating ring 46 extending upwardly from the plane of lip 44, so that the seal formed between lid 14 and body 12 is continuous.

In the preferred embodiment of lid 14, illustrated in FIG. 6, central portion 32 is of double wall construction, analagous to the preferred double wall structure of body 12 described above, having an inner wall 32$i$ and an outer wall 32$o$ disposed in parallel relation and defining a space 48 therebetween. The outer edges of walls 32$i$ and 32$o$ both intersect dome 36 at the outer edge 34 of lid 14 and are continuously interconnected thereto, sealing space 48 from the external environment. As with space 24 of the preferred embodiment of body 12, space 48 creates an insulating barrier to the transfer of heat from the interior of body 12 through lid 14. It is further preferred that space 48 be filled with an insulating material, designated as lid insulation 50, to increase the insulating efficiency of lid 14.

It is preferred that the structure of body insulation 26 and of lid insulation 50 be the same, although different structures may be used if desired. In their preferred embodiment, insulation 26 and 50 comprises a nonwoven fabric 52 bonded between an inner reflective sheet 54 and an outer reflective sheet 56, so as to insulate against heat loss through the insulating material by both conductive and radiant transfer. Sheets 54 and 56 are preferably thin sheets of a flexible plastic base material, such as polyester, with a thin layer of reflective material, such as aluminum, coated on at least one face thereof. If coated on only one face of each sheet, the reflective face of inner sheet 54 should be the face opposite the face in direct contact with fabric 52, and the reflective face of outer sheet 56 should be the face in contact with fabric 52, so that the reflective faces of the respective sheets will be directed toward the interior of basin 10. For reasons of economy, the outer sheet 56 may be omitted from the insulating material, but omission of that sheet will somewhat reduce the effectiveness of the insulation.

Body insulation 26 for each basin 10 is preferably formed with a configuration matching the configuration of body 12, and disposed in space 24 between walls 18$o$ and 18$i$ and between bottoms 20$o$ and 20$i$ during the construction of body 12. Alternatively, body insulation 26 may be formed as two components, one to be placed between walls 18$o$ and 18$i$, and one to be placed between bottom 20$o$ and 20$i$, if more convenient for construction. Lid insulation 50 is formed as a flat piece of insulating material of the same configuration and dimension as the central portion 32 of lid 14, to be disposed in space 48 during construction of lid 14.

It is often desireable for users of surgical basins to be able to visually inspect the liquid level within the basin for various reasons, and basin 10 is preferably provided with a graduated volume scale on the inner surface of side wall 18$i$. Because the preferred embodiment of the surgical irrigation basin of the invention is covered and insulated, body 12 may be provided with means of visually determining the volume of liquid contained therein without removal of lid 14. More specifically, body 12 may be formed of a transparent or suitably translucent material and provided with a pair of closely spaced elongate walls 58 extending longitudinally from the bottom of side wall 18 at bottom closure 20 over its outer surface to the lower surface of lip 44 in space 24 between walls 18*i* and 18*o*, as illustrated in FIG. 3. Walls 58 define a narrow strip of side wall 18 from which body insulation 26 is omitted. The uninsulated strip between walls 58 is provided with graduated scale 60, allowing a user to easily determine the volume of liquid within basin 10 without removing lid 14 and without significantly reducing the effect of body insulation 26.

Body 12, lid 14, and tube 16 are each preferably formed of an plastic material. In the preferred embodiments basin 10 is disposable and is intended for a single use, so the thickness of walls 18, bottoms 20, tube 16, and lid 14 need only be sufficient to maintain the integrity of basin 10 during that single use without concern for subsequent cleaning and sterilization. The material of construction of body 12 and lid 14 must be suitable for sterilization through any conventional sterilization method.

Although the preferred insulating material for body insulation 26 and lid insulation 50 is suitable for sterilization as well as providing efficient insulating properties with minimal thickness, the sealing of such insulating material within spaces 24 and 48 allows the use of insulating materials which are not suitable for sterilization and are thus not normally considered suitable for use in an operating room setting. It will thus be understood that almost any type of thin material having desirable insulating properties may be utilized in constructing basins of the preferred double wall design. It will also be understood that the advantages provided by flanged tube 16 may be achieved in an uninsulated basin of single wall design, as is depicted in FIG. 7, or may be achieved in a basin of single wall design surrounded by exposed insulating material of a type suitable for sterilization, as indicated in FIG. 8.

The foregoing description has been in terms of the insulated surgical irrigation basin embodiment, for illustration of the full range of features of the invention and not for purposes of limitation. The invention is susceptible to various modifications and further alternative embodiments without departing from the scope of the invention as claimed, such as an uninsulated surgical irrigation basin, an insulated covered basin without tube 16 for uses other than surgical irrigation, and insulated open top basins configured for various specialized medical uses, as illustrative examples. Various embodiments and variations of the basins of the invention may be packaged and provided together in sealed sterile packs for efficient and economical operating room preparation. As but one example, a useful package may contain a combination of the following: one large uninsulated, uncovered basin; one large insulated, covered basin; two graduated, insulated, covered surgical irrigation basins; one small insulated, uncovered basin; one uninsulated, uncovered emesis basin; and two small graduated, uninsulated, uncovered medicine cups.

What is claimed:

1. A surgical irrigation basin to contain a liquid irrigation solution and to be used in conjunction with an irrigation syringe, comprising a bowl-like open topped body having a continuous side wall with an upper edge defining a closed curve in a single plane, said side wall having an inner wall and an outer wall symmetrically spaced a short distance from said inner wall with said inner wall and said outer wall interconnected at said upper edge of said side wall and with each of said inner and outer walls having a lower edge, a bottom closure having an inner bottom and an outer bottom symmetrically spaced a short distance from said inner bottom, each of said inner bottom and said outer bottom having an outer edge, with the outer edge of said inner bottom interconnected to the lower edge of said inner wall in liquid-tight relation and with the outer edge of said outer bottom interconnected to the lower edge of said outer wall in liquid-tight relation, so as to form a fully enclosed space between the interconnected inner side wall and inner bottom and the interconnected outer side wall and outer bottom, with said upper edge of said side wall adapted to releaseably mate with a cover in liquid-tight relation;

a substantially planar cover having a central portion with an upper surface and a lower surface and having an outer edge, said central portion being of double wall construction with an inner wall and an outer wall symmetrically spaced a short distance from said inner wall, with said inner wall and said outer wall interconnected at said outer edge of said cover so as to form a fully enclosed space between said inner wall said outer wall of said central portion of said cover, said outer edge defining a closed curve in a single plane with said closed curve defined by said outer edge matching said closed curve defined by said upper edge of said side wall of said body, said outer edge adapted to releaseably mate with said upper edge of said wall of said body in liquid-tight relation for the purpose of releaseably interconnecting said cover to said body; and means forming a passageway from the exterior of the basin to the interior thereof for the purpose of inserting an irrigation syringe through the passageway to withdraw irrigation solution from the basin.

2. The surgical irrigation basin of claim 1, further comprising insulating material disposed within said space between said interconnected inner side wall and inner bottom and said interconnected outer side wall and outer bottom.

3. The surgical irrigation basin of claim 1, further comprising body insulating material disposed within said space between said interconnected inner side wall and inner bottom and said interconnected outer side wall and outer bottom, and lid insulating material disposed within said space between said inner wall and said outer wall of said central portion of said cover.

4. An insulated covered surgical irrigation basin, adapted for use in conjunction with an irrigation syringe for withdrawing irrigation solution from the basin, comprising an insulated bowl-like body having a continuous side wall with an upper edge defining a plane and a lower edge, a bottom closure with an outer edge, interconnected at its outer edge to the lower edge of said side wall in liquid-tight relation, first sealing means formed at said upper edge of said side wall, and body insulation interconnected to the outer surface of said body;

an insulated cover having a central portion with an outer edge of the same configuration and dimension as said upper edge of said side wall, second sealing means formed at and extending around said outer edge of said central portion and adapted to mate with said first sealing means of said body and releaseably interconnect said cover to said body in liquid-tight relation, cover insulation extending over and interconnected to the outer surface of said central portion, and an aperture penetrating said central portion, and said cover insulation interconnected thereto, at the outer edge of said central portion; and an open ended hollow tube with first and second ends, extending through said aperture penetrating said cover and said cover insulation and interconnected to said central portion in liquid-tight relation, with the first end of said tube extending a short distance outwardly from the outer surface of said cover and with the second end of said tube extending a short distance outwardly from the inner surface of said cover to form a passageway from the exterior of the basin to the interior thereof for insertion of an irrigation syringe.

5. The insulated covered surgical irrigation basin of claim 4, wherein said body insulation extends over the entire outer surface of said body in a thin layer of generally uniform thickness, said body further comprises a second side wall with an upper edge and a lower edge and a second bottom closure interconnected to the lower edge of said second side wall in liquid-tight relation, with said second side wall and second bottom closure disposed over said body insulation in concentric relation with the side wall and bottom closure of the body of claim 4, and with the upper edge of said second side wall interconnected to said first sealing means in liquid-tight relation so as to seal said body insulation between the side wall and bottom closure of the body of claim 4 and said second side wall and second bottom closure, and wherein said cover further comprises a second central portion disposed over said cover insulation in alignment with the central portion of said cover of claim 4, and interconnected to said second sealing means so as to seal said cover insulation between the central portion of the cover of claim 4 and said second central portion with said tube extending through both such central portions of said cover.

6. The insulated covered surgical irrigation basin of claim 4 wherein said first end of said tube is flared outwardly to form a flange to receive a portion of a bulb of an irrigation syringe extending through said tube.

7. The insulated covered surgical irrigation basin of claim 5 wherein the basin is constructed of materials suitable for sterilization and subsequent use in a human hospital surgical operating room, said body insulation and said cover insulation being formed of the same insulating material, comprising a fabric material having a thin sheet reflective to heat on one side thereof bonded to one side of said fabric material such that said reflective side of said thin sheet forms one exterior face of said insulating material, and said insulating material is disposed in said body and in said cover with said reflective side of said thin sheet facing toward the interior of the basin.

8. The insulated covered surgical irrigation basin of claim 7 wherein said insulating material further comprises a second thin sheet reflective to heat on one side thereof bonded to the opposite side of said fabric material with said reflective side of said second thin sheet in contact with said opposite side of said fabric material such that reflective sides of said thin sheet and said second thin sheet face in the same direction.

9. The insulated covered surgical irrigation basin of claim 5 wherein said first sealing means comprises a mating ring extending upwardly from and continuously around said upper edge of said side wall and an annular lip extending outwardly from and continuously around said upper edge of said side wall perpendicular to said mating ring, and wherein said second sealing means comprises a dome extending upwardly from and continuously around the outer edge of said central portion of said cover, a continuous slot extending into the interior of said dome from the lower surface thereof to receive said mating ring of said first sealing means, and an annular flange extending outwardly from and continuously around the outer surface of said dome perpendicular to said continuous slot, said flange to be received upon said lip when said cover is interconnected to said body.

10. The insulated covered surgical irrigation basin of claim 5, further comprising volumetric graduations formed on the inner surface of said side wall of said body.

11. The insulated covered surgical irrigation basin of claim 5, further comprising a pair of elongate walls disposed in parallel relation between said side wall of said body and said second side wall of said body and extending through the full height of said side walls perpendicular to the plane defined by said upper edge of said side wall, and volumetric graduations formed on one of said side walls between said pair of elongate walls, and wherein said side walls are formed of a substantially transparent material and said body insulation is omitted between said pair of elongate walls such that said volumetric graduations and liquid contained in said body are visible from the exterior of said body.

12. A covered insulated basin for medical use, comprising
a body having a first continuous side wall with an upper edge and a lower edge, a first bottom closure with an outer edge, interconnected at its outer edge to said lower edge of said first side wall in liquid-tight relation, further having a second continuous side wall with an upper edge and a lower edge, a second bottom closure with an outer edge, interconnected at its outer edge to said lower edge of said second side wall in liquid-tight relation, said first side wall and first bottom closure disposed within said second side wall and second bottom closure with a space between the outer surfaces of said first side wall and first bottom closure and the inner surface of said second side wall and second bottom closure and with said upper edge of said first side wall extending above said upper edge of said second side wall, and further having first sealing means to interconnect said first side wall to said second side wall and seal said space and adapted to mate with a cover, including an annular lip interconnected to said first side wall below said upper edge thereof and extending continuously around and outwardly therefrom over said upper edge of said second side wall and a short distance outwardly therefrom, said lip being interconnected to said upper edge of said second side wall; and
a cover having a first central portion with an outer edge and a second central portion with an outer edge, of the same configuration and dimension as said first central portion and disposed over and slightly separated from said first central portion so as to define a space therebetween, and second sealing means having a dome extending around the outer edges of said first and second central portions and interconnected thereto to seal said space between said first and second central portions, said dome having a continuous slot extending into the interior of said dome from the lower surface thereof to receive said upper edge of said first side wall of said body therein for the purpose of releaseably interconnecting said cover to said body in liquid-tight relation, said second sealing means further having an annular flange interconnected to and extending outwardly from said dome perpendicular to said slot, to be received upon said lip of said first sealing means when said cover is interconnected to said body.

13. The covered insulated basin of claim 12, further comprising body insulation disposed in the sealed space between said first side wall and first bottom closure and said second side wall and second bottom closure of said body.

14. The covered insulated basin of claim 13, further comprising cover insulation disposed in the sealed space between said first central portion and said second central portion of said body.

15. The covered insulated basin of claim 12, wherein said body further includes volumetric graduation markings formed on the inner surface of said first side wall.

16. The covered insulated basin of claim 12, wherein said body and said cover are formed of a plastic material suitable for sterilization.

* * * * *